United States Patent [19]

Busby et al.

[11] 4,317,879

[45] Mar. 2, 1982

[54] GLUCOSE ANALYZER MEMBRANE CONTAINING IMMOBILIZED GLUCOSE OXIDASE

[75] Inventors: Michael G. Busby, Madison; Diane E. Hartwig, Oregon, both of Wis.

[73] Assignee: Airco, Inc., Montvale, N.J.

[21] Appl. No.: 36,905

[22] Filed: May 7, 1979

[51] Int. Cl.³ .................. C12Q 1/26; C12Q 1/54; C12N 11/08
[52] U.S. Cl. .................. 435/14; 204/195 B; 435/25; 435/180; 435/182
[58] Field of Search .......... 435/14, 25, 180, 182, 435/188, 189, 190, 288; 204/195 B

[56] References Cited

U.S. PATENT DOCUMENTS

| | | | |
|---|---|---|---|
| 3,542,662 | 11/1970 | Hicks et al. | 435/190 X |
| 3,933,593 | 1/1976 | Sternberg | 435/14 |
| 3,972,274 | 9/1976 | Newman | 435/14 X |
| 4,004,979 | 1/1977 | Arvameas et al. | 435/181 X |

OTHER PUBLICATIONS

Updike et al, Continuous Glucose Monitor Based on an Immobilized Enzyme Electrode Detector, J. Lab. Clin. Med., vol. 93, No. 4, 4/79 (pp. 518–527).

*Primary Examiner*—David M. Naff
*Attorney, Agent, or Firm*—Roger M. Rathbun; Larry R. Cassett

[57] ABSTRACT

A membrane and the method of making the same is disclosed for use with glucose analyzers to detect the level of glucose in liquid mediums such as whole blood. The membrane comprises a thin base wafer of a hydrophobic fluorocarbon material such as polytetrafluoroethylene (TEFLON). The wafer is initially etched by removing surface fluorides to produce a hydrophilic surface and is then contacted with a mixed reagent formed by combining in a volume ratio of about 1:1:1 about 4% paraformaldehyde in water, about 5% bovine serum albumin in water and about 10% glucose oxidase in water. The resultant membrane contains glucose oxidase covalently bonded to the surface of the base wafer.

5 Claims, 1 Drawing Figure

GLUCOSE ANALYZER MEMBRANE CONTAINING IMMOBILIZED GLUCOSE OXIDASE

BACKGROUND OF INVENTION

This invention relates to analyzers for detecting levels of glucose in liquids such as whole blood, and, more particularly, to an improved membrane and method of making the same which can be used with such glucose analyzers.

Glucose analyzers have been developed which perform relatively rapid sampling of whole blood from a patient being monitored to analyze the same for glucose level. Such devices periodically withdraw such blood samples in vivo and allow attending personnel in hospitals to have a fairly current reading of the glucose levels of patients.

The purpose of such analyzers is to keep a constant track of such levels and are particularly useful with diabetic patients when transient glucose level spikes may give inadequate, or in some cases false indications of symptoms of certain patients, thus continuous monitoring can detect and qualify such false indications.

In addition, more frequent determinations are needed for glucose level when a diabetic patient is acutely ill, undergoing major surgery, childbirth or suffering from severe ketoacidosis.

The need for such continuously monitoring instruments has brought some to the market, but those face problems regarding precision, clotting and drift in blood sampling and detection systems and non-linearity of signal output.

A relatively new instrument has been proposed based on an immobilized enzyme electrode which operates in a rate detection mode. The enzyme electrode comprises a membrane having glucose oxidase bonded to a teflon wafer. One side of the membrane contacts the withdrawn whole blood while the other side is in contact with a polarographic electrode for detecting oxygen.

The instrument operates on the principal that, in the presence of glucose, oxygen tension rapidly falls as oxygen is consumed at the membrane end of the electrode. By observing and recording the rate of fall in oxygen tension, one can determine the glucose concentration due to the equation and the stoichiometric relationship between oxygen and glucose as follows:

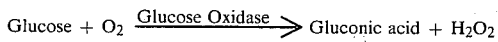
$$Glucose + O_2 \xrightarrow{Glucose\ Oxidase} Gluconic\ acid + H_2O_2$$

The immobilized enzyme membrane thus reacts, through the presence of glucose oxidase bonded to its surface, glucose and oxygen, and as the reaction proceeds, the polarographic electrode contacts the other surface of the membrane and gives off a signal as to the rate that the oxygen tension decreases. The membrane itself, being hydrophobic, prevents other liquids in the whole blood from passing through.

Such an instrument can achieve good specificity for oxygen since $O_2$ is the only electro-active substance in blood that will diffuse through Teflon, and specificity for glucose is also excellent due to the known specificity of glucose oxidase for glucose.

As can be readily seen, the membrane is an important component of such system, having an immobilized enzyme bonded to its surface in a manner to create a stable membrane to achieve reliable, repeatable results.

Such membranes have been known to use three particular reagents, paraformaldehyde, bovine serum albumin and glucose oxidase applied to a teflon base wafer having an etched surface, however, the particular proportions of the three reagents resulted in a membrane having relatively low shelf life, low activity and experienced problems in cracking of the enzyme coating during use.

In particular, a membrane was known by the inventions hereof which was produced by using solutions of 20% bovine serum albumin, 10% glucose oxidase and 4% paraformaldehyde in the respective proportions of 1:2:1 by volume. When tested in a commercial Beckman glucose analyzer such membranes showed activity evidenced by a reading of 61% of the gravimetric standard concentration. Their activity dropped about 23% in ten days, showing relatively poor shelf life. At the end of two weeks most of the membranes tested evidenced about 50% of their original activity.

SUMMARY OF INVENTION

There has been found specific optimized proportions for combining the three reagents, paraformaldehyde, bovine serum albumin and glucose oxidase and which significantly improves the important characteristics of the membrane. The membrane is made with a base wafer of a fluorocarbon hydrophobic material, preferably polytetrafluoroethylene (TEFLON). Specifically, the three reagents are prepared as follows: 40 mg paraformaldehyde dissolved in 960 $\mu$ of distilled water, 100 mg of bovine serum albumin dissolved in 1.9 ml of distilled water and 10 mg of glucose oxidase dissolved in approximately 90 microliters of distilled water are mixed separately and 100 microliters of each solution is mixed together, i.e. volume ratio of about 1:1:1. The final mixed reagent solution is placed on the etched surface of the wafer, air dried and then can be stored for a period of time before actual use. The resultant membrane, having been made of the mixed reagent solution of the foregoing ratio exhibits excellent shelf life and has a high activity without a severe cracking problem. By using the same test analyzer and procedures heretofore described the membranes produced readings of 70-80% of the gravimetric glucose standard. After storage for 37 days, the activity dropped only about 15%, thus having a commercially viable shelf life and activity.

DETAILED DESCRIPTION OF INVENTION

Figure 1:
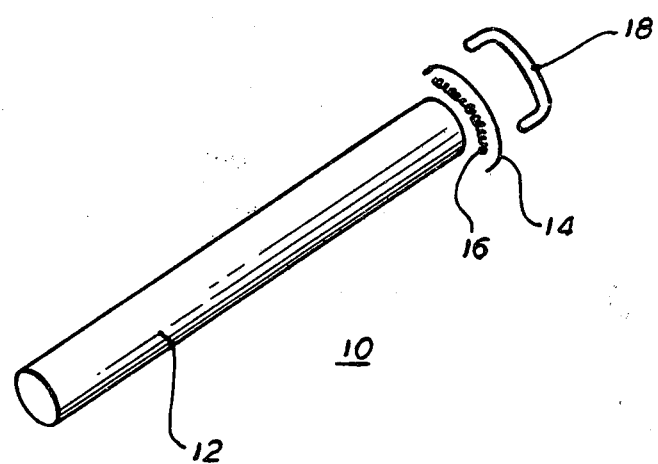
FIG. 1 is an isometric exploded view of an electrode using a membrane made in accordance with the present invention.

The membrane of the present invention, and the process for producing the same involve treating a fluorocarbon material with a reagent solution having specific proportions of individual reagents to produce a membrane having enhanced characteristics with respect to shelf life and chemical activity for glucose detector.

The membrane is preferably prepared on a polytetrafluoroethylene (TEFLON) wafer of approximately 25 micrometers thickness. The wafer is initially washed with distilled water and acetone and then allowed to air dry. The wafer is basically a hydrophobic material, i.e. it allows only gases to pass through the membrane while preventing liquids from passing therethrough. In practice, the use of a hydrophobic material allows only gases to thereby reach the polarographic electrode and therefor liquids, such as ascorbic acid found in whole blood, are prevented from interferring with the function of the electrode.

In order to make the wafer hydrophilic, its surface is etched to reactively remove surface fluorides from the fluoro carbon material. One suitable etchant that can be used is a sodium dispersion suspended in naphthalene, and sold commercially as Chemgrip Treating Agent by Chemplast, Inc. in Wayne, NJ. The etching step is accomplished by placing about two drops of the etchant in the center of the teflon wafer. After 10/20 seconds, the etching solution becomes clear and is washed with acetone. The resulting surface of the wafer is a brown stain when etching occurs and the surface itself is hydrophilic, having been stripped of fluorine atoms, leaving behind functional groups which facilitate bonding of the enzyme. The teflon wafer, having a derivatized surface is then washed with distilled water and allowed to dry in air.

A mixed reagent solution is prepared containing the enzyme to be surface bonded to the base wafer by combining three solutions of individual reagents. One of the reagent solutions is made up by mixing paraformaldehyde in water. As a specific example, and one that will be used herein to make up the specific desired proportion of individual reagents, 40 mg of paraformaldehyde is dissolved in approximately 960 $\mu$ of distilled water. Heat may be supplied to assist in bringing the formaldehyde into solution. A second reagent, bovine serum albumin is also prepared as a solution by dissolving about 100 mg in about 1.9 ml of distilled water. The third reagent is the enzyme, preferably glucose oxidase of the salt free lyophilized, fungal type available commercially from Cal Biochem of San Diego, CA. The glucose oxidase is also formed in solution by dissolving 10 mg in approximately 90 microliters of water with gentle swirling.

The three reagent solutions are then mixed together in a specific proportion of about 1:1:1. Preferably, the mixed reagent solution is now found by adding 100 microliters of the bovine serum albumin solution to 100 microliters of the glucose oxidase solution and the resultant mixture is gently swirled for about five minutes. To this mixed solution is added 100 microliters of the paraformaldehyde solution and again mixed by gentle swirling. The resultant mixed reagent solution is now complete and ready for applying to the derivatized surface of the teflon wafer. In the present form, the mixed reagent solution will remain stable for at least a two week period, if capped, and stored at about 4° C. There is sufficient quantity to produce 40–50 membranes.

The membrane is completed by placing a single drop of the mixed reagent solution on the derivatized surface of the TEFLON wafer and removing excess solution by means such as suction via a micropipet. The completed membrane can then be dried in air.

Storage of the membrane should be in a sealed container at about 4° C. and preferably in a 0.2 molar pH 6.0 phosphate buffer with 1% benzoic acid to retard bacterial growth.

Turning now to FIG. 1, there is shown an isometric, exploded view of an electrode for use in glucose analysis and illustrating the mounting of the membrane constructed in accordance with the present invention. The electrode 10 includes a basic polarographic electrode 12 which, in use, may be fitted within a cylindrical container. The membrane 14 is fitted over one end of the electrode 12 and covers that end. The membrane 14 is assembled in contact with the polarographic electrode 12 by means of a drop of electrolyte gel 16 that is spread over the end of the polarographic electrode 12 and which then has membrane 14 held against the polarographic electrode 12. The gel 16 may comprise potassium chloride saturated with silver chloride and such as readily available commercially from Beckman Instruments of Fullerton, CA. A cap 18 having a suitable opening in its center (not shown) may be snapped or otherwise fitted over the end of the polarographic electrode 12 and holds the membrane 14 tautly thereto.

In operation, the liquid containing the glucose is contacted with the outside surface of membrane 14 and, as explained, the polarographic electrode 12 senses the rate at which $O_2$ is used up, then providing a basis for determining glucose level in the liquid being sampled.

While the invention has been disclosed herein by reference to the details of preferred embodiments, it is to be understood that the disclosure is intended in an illustrative sense, and it is contemplated that modifications may be made in the process within the spirit of the invention and the scope of the appended claims.

We claim:

1. A composition for applying on a fluorocarbon treated to be hydrophillic to produce an immobilized glucose oxidase membrane for whole blood glucose analysis comprising:
    (a) a paraformaldehyde solution comprising about 4.0% paraformaldehyde in water;
    (b) a bovine serum albumin solution comprising about 5% bovine serum albumin in water; and
    (c) a glucose oxidase solution comprising about 10% glucose oxidase in water;
wherein each of the components (a), (b) and (c) are mixed together in a ratio of about 1:1:1.

2. A membrane for use with a polarographic electrode for detecting the level of glucose in a liquid, said membrane comprising a base wafer of a fluorocarbon hydrophobic material, said wafer having bonded thereto a mixed reagent produced by combining (a) paraformaldehyde solution comprising about 4% paraformaldehyde in water, (b) a bovine serum albumin solution comprising about 5% bovine serum albumin in water, and (c) a glucose oxidase solution comprising about 10% glucose oxidase in water in the respective proportions of 1:1:1 by volume.

3. A membrane as defined in claim 2 wherein said hydrophobic material is polytetrafluoroethylene.

4. A method of producing a membrane for use with a polargraphic electrode for detecting the level of glucose in a liquid, said method comprising:
    (a) preparing a solution by combining about 4% paraformaldehyde in water,
    (b) preparing a solution by combining about 5% bovine serum albumin in water,
    (c) preparing a solution by combining about 10% glucose oxidase in water,
    (d) mixing the solutions of (a), (b) and (c) together in relative proportions of 1:1:1 by volume, and
    (e) preparing a base wafer of a fluorocarbon material and etching the surface thereof to remove surface fluorides, and
    (f) bonding said mixed solution of step (d) to the etched surface of the fluorocarbon material.

5. A method as defined in claim 4 wherein said fluorocarbon material is polytetrafluoroethylene.

* * * * *